US005512696A

United States Patent [19]

Kreutzer et al.

[11] Patent Number: 5,512,696
[45] Date of Patent: Apr. 30, 1996

[54] HYDROCYANATION PROCESS AND MULTIDENTATE PHOSPHITE AND NICKEL CATALYST COMPOSITION THEREFOR

[75] Inventors: Kristina A. Kreutzer, Wilmington, Del.; Wilson Tam, Boothwyn, Pa.

[73] Assignee: E. I. Du Pont de Nemours and Company, Wilmington, Del.

[21] Appl. No.: 505,137

[22] Filed: Jul. 21, 1995

[51] Int. Cl.⁶ .................................................. C07C 253/10
[52] U.S. Cl. .................. 558/338; 502/162; 502/164; 502/165
[58] Field of Search .................................... 558/338

[56] References Cited

U.S. PATENT DOCUMENTS

| | | | |
|---|---|---|---|
| 3,496,210 | 2/1970 | Drinkard, Jr. et al. | 260/465 |
| 3,496,215 | 2/1970 | Drinkard, Jr. et al. | 260/465.8 |
| 3,496,217 | 2/1970 | Drinkard, Jr. et al. | 260/465 |
| 3,496,218 | 2/1970 | Drinkard, Jr. | 260/465.8 |
| 3,536,748 | 10/1970 | Drinkard, Jr. et al. | 260/465.9 |
| 3,547,942 | 12/1970 | Godefroi et al. | 260/309 |
| 3,574,701 | 4/1971 | Kominami et al. | 260/465.3 |
| 3,578,695 | 5/1971 | Milberger et al. | 260/465.3 |
| 3,584,029 | 6/1971 | Kominami et al. | 260/465.3 |
| 3,631,191 | 12/1971 | Kane et al. | 260/439 |
| 3,655,723 | 4/1972 | Drinkard, Jr. | 260/465.3 |
| 3,676,481 | 7/1972 | Chia | 260/465.9 |
| 3,739,011 | 6/1973 | Drinkard, Jr. | 558/355 |
| 3,766,231 | 10/1973 | Gosser et al. | 260/439 R |
| 3,766,237 | 10/1973 | Chia et al. | 260/465.3 |
| 3,773,809 | 11/1973 | Walter | 260/465.8 |
| 3,775,461 | 11/1973 | Drinkard et al. | 260/465.3 |
| 3,798,256 | 3/1974 | King et al. | 558/338 |
| 3,846,461 | 11/1974 | Shook, Jr. | 260/439 R |
| 3,847,959 | 11/1974 | Shook, Jr. et al. | 260/439 R |
| 3,852,325 | 12/1974 | King | 558/355 |
| 3,852,328 | 12/1974 | Chia et al. | 558/355 |
| 3,852,329 | 12/1974 | Tomlinson | 558/355 |
| 3,853,948 | 12/1974 | Drinkard, Jr. et al. | 558/355 |
| 3,865,864 | 2/1975 | Nakajima et al. | 260/465.3 |
| 3,869,500 | 3/1975 | Kominami et al. | 260/465.3 |
| 3,903,120 | 9/1975 | Shook, Jr. et al. | 260/439 R |
| 3,925,445 | 12/1975 | King et al. | 558/338 |
| 4,298,546 | 11/1981 | McGill | 558/355 |
| 4,371,474 | 2/1983 | Rapoport | 558/338 |
| 4,599,206 | 7/1986 | Billig et al. | 558/85 |
| 4,668,651 | 5/1987 | Bilig et al. | 502/158 |
| 4,688,651 | 8/1987 | Dysart | 175/371 |
| 4,705,881 | 11/1987 | Rapoport | 558/338 |
| 4,714,773 | 12/1987 | Rapoport | 558/338 |
| 4,717,775 | 1/1988 | Billig et al. | 568/454 |
| 4,769,498 | 9/1988 | Billig et al. | 568/454 |
| 4,774,353 | 9/1988 | Hall et al. | 558/335 |
| 4,783,546 | 11/1988 | Burke et al. | 558/355 |
| 4,874,884 | 10/1989 | McKinney et al. | 558/338 |
| 5,202,297 | 4/1993 | Lorz et al. | 502/106 |
| 5,235,113 | 8/1993 | Sato et al. | 568/454 |
| 5,312,957 | 5/1994 | Casalnuovo et al. | 558/410 |
| 5,440,067 | 8/1995 | Druliner | 558/355 |
| 5,449,807 | 9/1995 | Druliner | 558/355 |

FOREIGN PATENT DOCUMENTS

| | | |
|---|---|---|
| 0518241 | 12/1992 | European Pat. Off. . |
| 6916495 | 5/1971 | Netherlands . |
| 1417554 | 12/1975 | United Kingdom . |
| WO85/03702 | 8/1985 | WIPO . |
| WO93/03839 | 3/1993 | WIPO . |

OTHER PUBLICATIONS

Cuny, G. D. et al, "Practical, High–Yield, Regioselective, Rhodium–Catalyzed Hydroformylation of Functionalized α–Olefins", *J. Am. Chem. Soc.*, 115, pp. 2066–2068 (1993).

Burgstahler, A. W. et al., "Improved Modification of the Rosenmund Reduction," *Synthesis*, pp. 767–768 (1976).

Tolman, C. A. et al, "Homogeneous Nickel–Catalyzed Olefin Hydrocyanation", *Advances in Catalysis*, 33 pp. 1–46 (1985).

Baker, M. J. et al, "Chelating Diphosphite Complexes of Nickel(0) and Platinum(0): Their Remarkable Stability and Hydrocyanation Activity", *J. Chem. Soc., Chem. Commun.*, pp. 803–804 (1991).

Baker, M. J. et al., "Chiral Aryl Diphosphites: A New Class of Ligands for Hydrocyanation Catalysis", *J. Chem. Soc., Chem. Communi.*, pp. 1292–1293 (1991).

Seidel, W. C. et al., "Ethylene[bis(tri–o–tolyl phosphite)] nickel(0)", *Inorganic Chemistry*, 9(10), pp. 2354–2357 (1970).

Kurokawa, H. et al. "Skeletal Rearrangement of Unsaturated Nitriles over Solid–Base Catalysts", *J. of Catalysis*, 141, pp. 94–101 (1993).

Pastor, S. D. et al, "Conformation of Eight–Membered Dioxathiasilocin Heterocycles in Solution", *Phosphorus and Sulfur*, 32, pp. 105–111 (1987).

Yamada, F. et al, "Substituted Bisphenols as Antioxidants for Autoxidation of Tetralin", *Bull. Chem. Soc. Japan*, 62, pp. 3603–3608 (1989).

*Primary Examiner*—Joseph Paul Brust

[57] ABSTRACT

A process for hydrocyanation of an aliphatic monoethylenically unsaturated compound, in which the ethylenic double bond is not conjugated to any other unsaturated group in the molecule, or a monoethylenically unsaturated compound in which the ethylenic double bond is conjugated to an ester group, which process uses a catalyst composition comprising a zero-valent and a multidentate phosphite ligand in the presence of a Lewis acid promoter.

8 Claims, No Drawings

HYDROCYANATION PROCESS AND MULTIDENTATE PHOSPHITE AND NICKEL CATALYST COMPOSITION THEREFOR

FIELD OF THE INVENTION

The invention relates to a process and catalyst composition for the hydrocyanation of monoethylenically unsaturated compounds wherein zero-valent nickel and a multidentate phosphite ligand are used in the presence of a Lewis acid promoter.

BACKGROUND OF THE INVENTION

Hydrocyanation catalyst systems, particularly pertaining to the hydrocyanation of ethylenically unsaturated compounds, are known in the art. For example, systems useful for the hydrocyanation of butadiene to form penetenenitrile (PN) and in the subsequent hydrocyanation of penetenenitrile to form adiponitrile (ADN), are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723; and 3,766,237, and Tolman et al., Advances in Catalysis, 33, 1, 1985. The hydrocyanation of activated ethylenically unsaturated compounds, such as with conjugated ethylenically unsaturated compounds (e.g., butadiene and styrene), and strained ethylenically unsaturated compounds (e.g., norbornene) proceeds without the use of a Lewis acid promoter, while hydrocyanation of unactivated ethylenically unsaturated compounds, such as 1-octene and 3-pentenenitrile, requires the use of a Lewis acid promoter.

Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. Moreover, U.S. Pat. No. 4,874,884 discloses for producing ADN by the zero-valent nickel-catalyzed hydrocyanation of pentenenitriles in the presence of a synergistic combination of promoters selected in accordance with the reaction kinetics of the ADN synthesis.

Phosphite ligands have been shown to be useful ligands in the hydrocyanation of activated ethylenically unsaturated compounds. See, for example, Baker, M. J., and Pringle, P. G., J. Chem. Soc., Chem. Commun., 1292, 1991; Baker et al., J. Chem. Soc., Chem. Commun., 803, 1991; Union Carbide, WO 93,03839. Also, phosphite ligands have been disclosed with rhodium in the hydroformylation of functionalized ethylenically unsaturated compounds: see, Cuny et al., J. Am. Chem. Soc., 1993, 115, 2066.

The present invention provides a novel process and catalyst precusor complex which is more rapid, selective, efficient and stable than current processes and catalyst complexes employed in the hydrocyanation of monoethylenically unsaturated compounds. Other objects and advantages of the present invention will become apparent to those skilled in the art upon reference to the detailed description of the invention which hereinafter follows.

SUMMARY OF THE INVENTION

The present invention provides a hydrocyanation process, comprising reacting an acyclic, aliphatic, monoethylenically unsaturated compound in which the ethylenic double bond is not conjugated to any other olefinic group in the molecule, or a monoethylenically unsaturated compound in which the ethylenic double bond is conjugated to an organic ester group, with a source of HCN in the presence of a catalyst precursor composition comprising a Lewis acid, a zero-valent nickel, and at least one multidentate phosphite ligand selected from the group represented by the following Formulas I, II, III, IV, V, VI, and VII, in which all like reference characters have the same meaning, except as further explicitly limited.

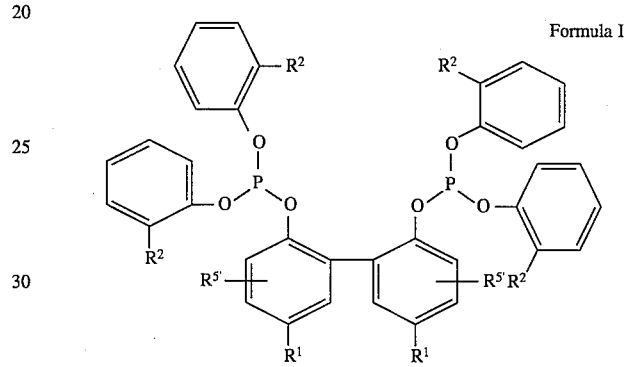

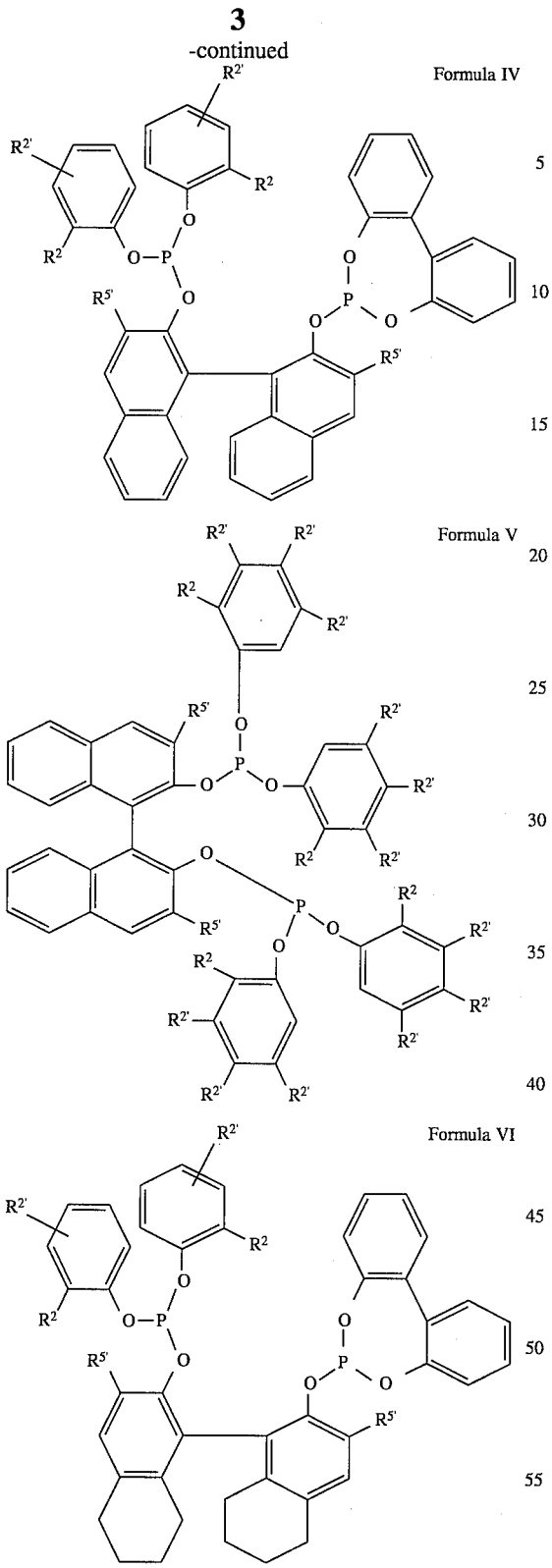

Formula IV

Formula V

Formula VI

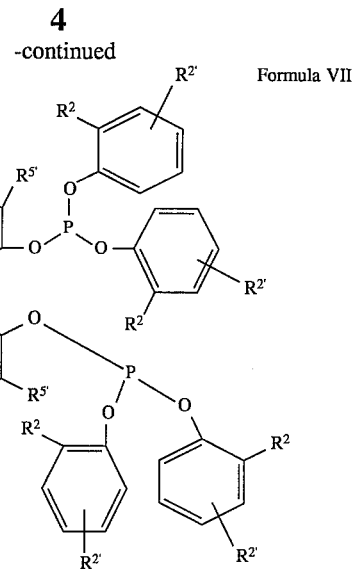

Formula VII wherein
- each $R^1$ is independently, H, halogen, a $C_1$ to $C_6$ alkyl, or $OR^3$ wherein $R^3$ is a $C_1$ to $C_6$ alkyl;
- each $R^2$ is independently a secondary or tertiary hydrocarbyl of 3 to 6 carbon atoms;
- each $R^{2'}$ is independently H, halogen, $OR^3$ wherein $R^3$ is a $C_1$ to $C_6$ alkyl or a primary, secondary or tertiary hydrocarbyl of 1 to 6 carbon atoms; for Formula II, III, VI, VI and VII, $R^{2'}$ is at either the meta or para position to the oxygen;
- each $R^{5'}$ is independently H or a primary or secondary hydrocarbyl of 1 or 3 carbon atoms in either the ortho or meta position to the oxygen or $CO_2R^{3'}$ wherein $R^{3'}$ is a $C_1$ to $C_4$ alkyl; and
- each X is independently O or $CH(R^{4'})$, wherein $R^{4'}$ is H, a substituted phenyl, or a $C_1$ to $C_6$ alkyl;
  - with the proviso that the terms "secondary" and "tertiary" herein refer to the carbon atom bonded to an aromatic ring;
  - and with the further proviso that in Formulas I, II, and V at least one $R^2$ cannot be a tertiary hydrocarbyl.

In the above catalyst compositions, the Lewis acid is considered to be a promoter.

The present invention further provides a catalyst composition consisting essentially of zero-valent nickel and at least one multidentate phosphate ligand selected from one of Formula I, II, III, IV, V, VI and VII, as defined above.

DETAILED DESCRIPTION OF THE PREFERRED EMBODIMENTS

Representative ethylenically unsaturated compounds which are useful in the process of this invention are shown in Formula VIII or X, and the corresponding terminal nitrile compounds produced are illustrated by Formulas IX or XI, respectively, wherein like reference characters have same meaning.

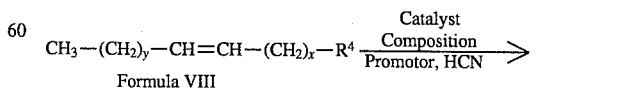

Formula VIII

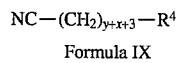

Formula IX or

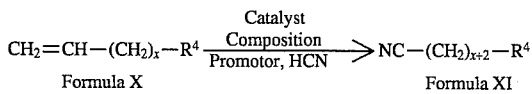

Formula X      Formula XI wherein
$R^4$ is H, CN, $CO_2R^5$, or perfluoroalkyl;
y is an integer of 0 to 12;
x is an integer of 0 to 12 when $R^4$ is H, $CO_2R^5$ or perfluoroalkyl;
x is an integer of 1 to 12 when $R^4$ is CN; and
$R^5$ is alkyl.

One of the ligands useful in the catalyst compositions of the present invention is illustrated above by Formula I, as defined. Alkyl groups in Formula I can be either straight chain or branched. When $R^1$ is $OR^3$, $R^3$ can be primary, secondary or tertiary; examples include methyl, ethyl, isopropyl and t-butyl. In the preferred ligand, both $R^1$ groups are H, methoxy groups, or chlorine. As stated in the definitions of the reference characters, all of the $R^2$ groups in Formula I cannot be tertiary hydrocarbyls; see Comparative Example 3 for Ligand "A2". The term "hydrocarbyl" is well known to the art and designates a hydrocarbon molecule from which one hydrogen atom has been removed. Such structure can contain single, double, or triple bonds. In the preferred Formula I ligand, $R^2$ in each occurrence is isopropyl, $R^1$ is methoxy, and $R^{5'}$ is hydrogen. In Formula II, X preferably is CH(Et), where Et stands for ethyl, $R^2$ in each occurrence is isopropyl, $R^{2'}$ is hydrogen, and each one of $R^1$ and $R^{5'}$ is methyl, where each $R^{5'}$ is in a position ortho to the oxygen atom. Again, all of the $R^2$ groups cannot be tertiary hydrocarbyls; see Comparative Example 13 for Ligand "J2". In the preferred Formula III ligand, each $R^2$ is isopropyl, each $R^{2'}$ is hydrogen, X is $CHR^{4'}$, where $R^{4'}$ is 4-methoxyphenyl, and each $R^{5'}$ is hydrogen. In the preferred Formula IV ligand, each $R^2$ group is isopropyl, and each $R^{2'}$ and $R^{5'}$ is hydrogen. In the preferred Formula V ligand, each $R^2$ group is isopropyl, each $R^{2'}$ group is para to $R^2$ methyl with the other $R^{2'}$ being hydrogens and each $R^{5'}$ is hydrogen. In the preferred Formula VI ligand, each $R^2$ group is isopropyl, each $R^{2'}$ is hydrogen, and each $R^{5'}$ is hydrogen. In the preferred Formula VII ligand, each $R^2$ group is isopropyl, and each $R^{2'}$ group is hydrogen and each $R^{5'}$ group is hydrogen.

The catalyst composition of the invention may be considered a "precursor" composition in that the zero-valent nickel at some point becomes complexed to the multidentate, phosphite ligand, and, further in all likelihood, additional reactions occur during hydrocyanation, such as, for example, complexing of the initial catalyst composition to an ethylenically unsaturated compound.

These ligands can be prepared by a variety of methods known in the art, for example, see descriptions in European Patent Application 92109599.8 of Mitsubishi Kasei Corporation and the corresponding U.S. Pat. No. 5,235,113 to Sato et al. The reaction of 2-isopropylphenol with phosphorus trichloride gives the phosphorochloridite. The reaction of this phosphorochloridite with 2,2'-dihydroxy- 5,5'-dimethyoxy-1,1'-biphenyl in the presence of triethylamine gives the above-identified preferred ligand of Formula I.

The zero-valent nickel compounds can be prepared or generated according to techniques well known in the art, as described, for example U.S. Pat. Nos. 3,496,217; 3,631,191; 3,846,461; 3,847,959; and 3,903,120, which are incorporated herein by reference. Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni(P(O\text{-}o\text{-}C_6H_4CH_3)_3)_2(C_2H_4)$, both of which are known in the art. Alternatively, divalent nickel compounds may be combined with a reducing agent, to serve as a source of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Z, Fe, Al, Na, or $H_2$. Elemental nickel, preferably nickel powder, when combined with a halogenated catalyst, as described in U.S. Pat. No. 3,903,120, is also a suitable source of zero-valent nickel.

The nonconjugated acyclic, aliphatic, monoethylenically unsaturated starting materials useful in this invention include unsaturated organic compounds containing from 2 to approximately 30 carbon atoms. 3-pentenenitrile and 4-pentenenitrile are especially preferred. As a practical matter, when the nonconjugated acyclic aliphatic monoethylenically unsaturated compounds are used in accordance with this invention, up to about 10% by weight of the monoethylenically unsaturated compound may be present in the form of a conjugated isomer, which itself may undergo hydrocyanation. For example, when 3-pentenenitrile is used, as much as 10% by weight thereof may be 2-penetenenitrile. (As used herein, the term "pentenenitrile" is intended to be identical with "cyanobutene"). Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc., nonconjugated diethylenically unsaturated compounds such as allene, substituted compounds such as 3-pentenenitrile, 4-pentenenitrile, methyl pent-3-enoate, and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

The starting ethylenically unsaturated compounds useful in this invention and the hydrocyanation products thereof are those shown above in Formulas VII through XI. Those of Formula VIII yield terminal nitriles of Formula IX, while those of Formula X yield terminal nitriles of Formula XI.

Preferred are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH=CH_2$ (where z is 1 to 12).

The preferred products are terminal alkanenitriles, linear dicyanoalkylenes, linear aliphatic cyanoesters, and 3-(perfluoroalkyl)propionitrile. Most preferred products are adiponitrile, alkyl 5-cyanovalerate, $C_zF_{2z+1}CH_2CH_2CN$, where z is 1 to 12.

The present hydrocyanation process may be carried out, for example, by charging a reactor with the reactants, catalyst composition, and solvent, if any; but preferably, the hydrogen cyanide is added slowly to the mixture of the other components of the reaction. Hydrogen cyanide may be delivered as a liquid or as a vapor to the reaction. Another suitable technique is to charge the reactor with the catalyst and the solvent to be used, and feed both the unsaturated compound and the HCN slowly to the reaction mixture. The molar ratio of unsaturated compound to catalyst can be varied from about 10:1 to about 2000:1.

Preferably, the reaction medium is agitated, for example, by stirring or shaking. The reaction product can be recovered by conventional techniques such as, for example, by distillation. The reaction may be run either batchwise or in a continuous manner.

The hydrocyanation reaction can be carried out with or without a solvent. The solvent, if used, should be liquid at the reaction temperature and pressure and inert towards the unsaturated compound and the catalyst. Suitable solvents include hydrocarbons, such as benzene or xylene, and nitriles, such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from $-25°$ C. to $200°$ C. can be used, the range of $0°$ C. to $150°$ C. being preferred.

Atmospheric pressure is satisfactory for carrying out the present invention and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

EXAMPLES

The following non-limiting, representative examples illustrate the process and catalyst compositions of this invention. All parts, proportions, and percentages are by weight, unless otherwise indicated. In each example, the following procedure was used unless otherwise noted.

The mixtures were heated in a thermostatically controlled oil bath. HCN was delivered to the flask as an $HCN/N_2$ gas mixture by bubbling dry nitrogen carrier gas through liquid HCN maintained in an ice bath at $0°$ C. This provided a vapor stream which was about 35% HCN (vol/vol). Samples were periodically analyzed by gas chromatography (GC). In the examples, ADN stands for adiponitrile, MGN stands for 2-methylglutaronitrile, and ESN stands for ethylsuccinonitrile. COD stands for bis(1,5-cyclooctadiene) and THF stands for tetrahydrofuran.

Example 1

Synthesis of the ligand of Formula I where each $R^2$ is isopropyl and each $R^1$ is H (Ligand "A")

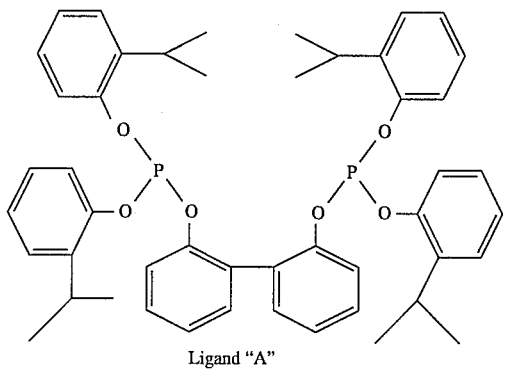

Ligand "A"

To a solution of 2.0 g of phosphochloridite derived from $PCl_3$ and 2-isopropylphenol in 20 ml of toluene was added 0.55 g (2.95 mmoles) of 2,2'-biphenol and 1.1 g (10.9 mmoles) of $NEt_3$ in 20 ml of toluene. After stirring overnight under nitrogen, the mixture was filtered through Celite® (a product of Johns-Manville Company), and washed with toluene. The remaining solvent was removed in a rotary evaporator. Thus was obtained 2.163 g of product as an opaque liquid. $^{31}P$ {1H} (121.4 MHz, $C_6D_6$): 130.96 ppm. $^1H$ (300 MHz, $C_6D_6$): 7.51 (d, J=8Hz, 2H), 7.39 (dd, J=1.6, 7.5 Hz, 2H), 7.2–6.9 (m, 20H), 3.43 (septet, J=6.9 Hz, 4H), 1.19 (d, J=6.9 Hz, 24H) along with a small amount of toluene. HRMS (High Resolution Mass Spectroscopy) calculated for $C_{48}H_{52}O_6P_2$: 786.3239; Found: 786.3208.

Example 1A

Hydrocyanation of 3-Pentenenitrile with Ligand "A"/$Ni(COD)_2$; $ZnCl_2$ promoter 342 mg of Ligand "A" and 40 mg $Ni(COD)_2$ were dissolved in 5 ml THF. The solvent was removed by vacuum evaporation and 5 ml of 3PN (3-pentenenitrile) and 20 mg of $ZnCl_2$ were added. The mixture was treated with HCN at a nitrogen carrier gas flow rate of 12 ml/min at $50°$ C. for 15 minutes. After this time, the temperature controller was set at $60°$ C. At 15 minute intervals, the temperature was increased to $70°$, $80°$, and $100°$ C. Fifteen minutes after a temperature of $100°$ C. was set, GC analysis indicated 46.7% ADN, 8.0% MGN, and 1.0% ESN.

Example 1B

Hydrocyanation of 3-Pentenenitrile with Ligand "A"/$Ni(COD)_2$; $ZnCl_2$ promoter Ligand "A", 332 mg, and 40 mg of $Ni(COD)_2$ were dissolved in 5 ml of THF. The solvent was removed by vacuum evaporation; then, 5 ml of 3PN and 20 mg of $ZnCl_2$ were added. The mixture was treated with HCN with a nitrogen carrier gas flow rate of 12 ml/min at $70°$ C. for 2 hrs. GC analysis indicated 70.0% ADN, 11.6% MGN and 1.4% ESN (selectivity to ADN: 84%).

Example 1C

Hydrocyanation of 3-Pentenenitrile with Ligand "A"/Ni(COD)₂; ZnCl₂ promoter Ligand "A", 330 mg, and 40 mg of Ni(COD)₂ were dissolved in 5 ml of THF. The solvent was removed by vacuum evaporation, and 5 ml of 3PN and 20 mg of ZnCl₂ were added. The mixture was treated with HCN with a nitrogen carrier gas flow rate of 30 ml/min at 70° C. for one hour. After this time, GC analysis indicated 26.4% ADN, 4.5% MGN and 0.6% ESN (selectivity to ADN: 84).

Example 2

Synthesis of the ligand of Formula I where each $R^2$ is isopropyl, each $R^{5'}$ is H, and each $R^1$ is $OCH_3$ (Ligand "B")

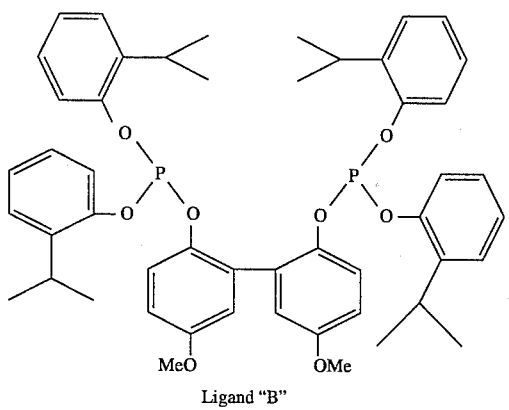

Ligand "B"

2,2'-Dihydroxyl-5,5'-dimethoxy-1,1'-biphenyl was prepared by the dealkylation of 2,2'-dihydroxy-3,3'-di-t-butyl-5,5'-dimethoxy-1,1'-biphenyl using a procedure described in the literature (Tashiro et al., Organic Preparations and Procedures Int., 8, 263, 1976). Ten grams of AlCl₃ and 10 g of 2,2'-dihydroxy-3,3'-di-t-butyl-5,5'-dimethoxy-1,1'-biphenyl were mixed in 125 ml of benzene and heated at 40° C. for 3 hours. The mixture was cooled in ice, and 125 ml of 10% aqueous HCl was added slowly. The organic layer was separated and washed with three 125-ml portions of 10% NaOH. The basic solution was neutralized with concentrated HCl and extracted three times with 100 ml portions of ether. The ether layer was dried over Na₂SO₄. After filtering and removing the solvent by vacuum evaporation, the brown oil was washed with hexane; the product crystallized from CH₂Cl₂/hexane, yielding 2.202 g of 2,2'-dihydroxy-5,5'-dimethyoxy-1,1'-biphenyl, which was obtained as a white solid. ¹H (300 MHz, CD₂Cl₂): 6.9–6.8 (m, 6H), 5.71 (s, 2H), 3.78 (s, 6H).

To 2 g of phosphochloridite derived from PCl₃ and 2-isopropylphenol in 20 ml of toluene was added 660 mg of the 2,2'-dihydroxy-5,5'-dimethyoxy-1,1'-biphenyl prepared above and 1.01 g of NEt₃ in 20 ml of toluene. The mixture was stirred overnight and filtered through Celite®, and washed with toluene. The solvent was removed to give 2.588 g of the desired product as an orange oil. ³¹P {1H} (121.4 MHz, C₆D₆): 131.41. ¹H NMR (Nuclear Magnetic Resonance) (C₆D₆): 7.4–6.4 (22H), 3.3 (m, 4H), 3.1 (s, 6H), 1.0 (m, 24H) along with a small amount of toluene. FBMS (Fast Atom Bombardment Mass Spectroscopy): calculated M-OCH₃: 815.36; Found: 815.07.

Example 2A

Hydrocyanations of 3-Pentenenitrile with Ligand "B"/Ni(o-TTP)₂(C₂H₄), where o-TTP is P(O-o-C₆H₄CH₃)₃; ZnCl₂ promoter Ligand "B", 346 mg, 0.111 g of Ni(o-TTP)₂(C₂H₄), and 20 mg of ZnCl₂ were dissolved in 5 ml of 3PN. The mixture was treated with HCN at a nitrogen carrier gas flow rate of 30 ml/min at 70° C. for one hour. GC analysis indicated 61.2% ADN, 9.9% MGN and 1.3% ESN (selectively to ADN: 84.5%).

Comparative Examples 3–4A Biphenol Backbone
Comparative Example 3

Synthesis of the Ligand of Formula I where all $R_2$ are t-butyl, a t-butyl group is meta to each $R^2$, and $R^1$ and $R^5$ are H (Ligand "A2")

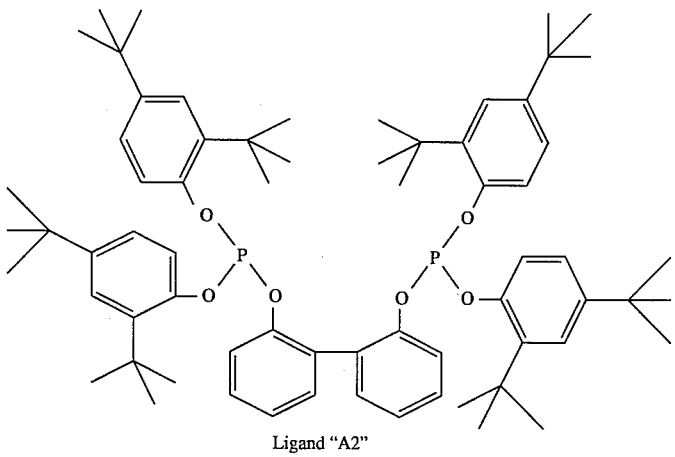

Ligand "A2"

To 3.8 g of the chlorodite derived from PCl₃ and 2,4-di-t-butylphenol in 20 ml of toluene there was added 0.75 g of 2,2'-biphenol and 0.809 g of NEt₃ in 20 ml of toluene. The mixture was stirred overnight and then filtered through Celite® and washed with toluene. The solvent was removed in a rotary evaporator. The residue was washed with acetonitrile, and filtered to give 1.381 g of the product as a white solid. ³¹P {1H} (121.4 MHz, C₆D₆): 132.46 ppm. Also, small peaks at 161.57 and 139.88 due to impurities.

Comparative Example 3A

Hydrocyanation using Ligand "A2" and Ni(o-TTP)$_2$(C$_2$H$_4$)

Ligand "A2", 448 mg, and 0.111 g of Ni(o-TTP)$_2$(C$_2$H$_4$) and 20 mg of ZnCl$_2$ were dissolved in 5 ml of 3PN. The mixture was treated with HCN at a nitrogen carrier gas flow rate of 30 ml/min at 70° C. for one hour. GC analysis indicated 0.0% ADN, 0.05% MGN and 0.1% ESN.

Comparative Example 3B

Hydrocyanation using Ligand "A2" and Ni(COD)$_2$

Ligand "A2", 452 mg, 0.040 g of Ni(COD)$_2$, and 20 mg of ZnCl$_2$ were dissolved in 5 ml of 3PN. The mixture was treated with HCN at a nitrogen carrier gas flow rate of 30 ml/min at 70° C. for one hour. GC analysis indicated 0.0% ADN, 0.0% MGN, and 0.1% ESN.

Comparative Example 4

Synthesis of the Ligand of Formula I where R$^2$ is —CH$_3$ and R$^1$ and R$^{5'}$ and H (Ligand "A3")

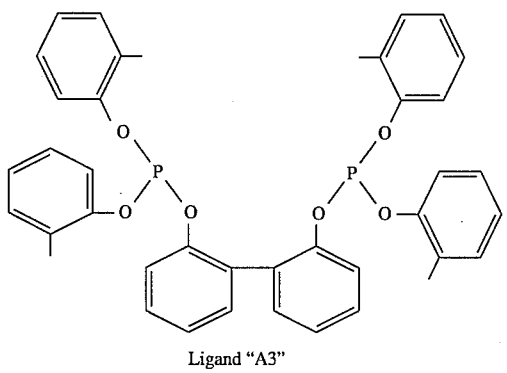

Ligand "A3"

The phosphachloridite was prepared in the usual manner by the reaction of PCl$_3$ with o-cresol at 0° C. in toluene, followed by fractional distillation at reduced pressure. It (1.85 g; 6.6 mmol) was dissolved in toluene (30 ml), and the solution was cooled to 0° C. Triethylamine (3 ml) was added, followed by 2,2'-biphenol (0.56 g, 3.0 mmols). The mixture was stirred overnight at room temperature. The solids were filtered, and the solvent was removed at a reduced pressure to give 2.26 g of an lightly orange-colored liquid. $^{31}$P NMR (CDCl$_3$): δ133.1. Also, smaller peaks at 144.5, 131.2, and 3.2 due to impurities. $^1$H NMR also indicated a small amount of Et$_3$N/salts.

Comparative Example 4A

Hydrocyanation using Ligand "A3"

Ligand "A3,", 346 mg, 0.111 g of Ni(o-TTP)$_2$(C$_2$H$_4$), and 20 mg of ZnCl$_2$ were dissolved in 5 ml of 3PN. The mixture was treated with HCN at a nitrogen carrier gas flow rate of 30 ml/min at 70° C. for one hour. GC analysis indicated 0.0% ADN, 0.05% MGN and 0.0% ESN.

Example 5

Synthesis of the ligand of Formula II where each R$^2$ is isopropyl, each R$^1$, R$^{2'}$ and R$^{5'}$ is H, and X is —CH$_2$— (Ligand "C")

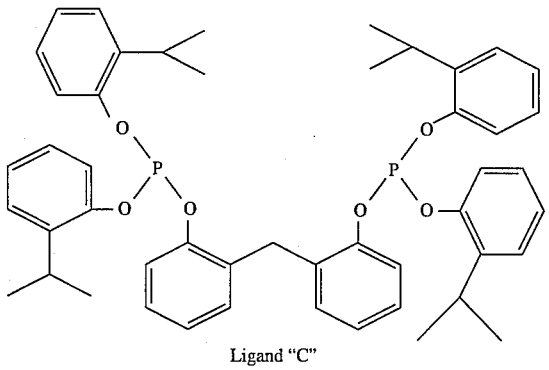

Ligand "C"

To 2 g of the phosphochloridite derived from PCl$_3$ with 2-isopropylphenol in 20 ml of toluene there was added 595 mg of bis(2-hydroxyphenyl)methane and 1.01 g of NEt$_3$ in 20 ml of toluene. The mixture was stirred overnight, filtered through Celite®, and washed with toluene. The solvent was removed, to give 2.514 g of the desired product as a pale yellow oil. $^{31}$P {1H} (121.4 MHz, C$_6$D$_6$): 131.33. $^1$H NMR (C$_6$D$_6$): 4.11 (s, 2H), 3.2 (m, 4H), 0.98 (d, 24H) along with aromatic resonances and a little toluene. HRMS: calculated C$_{49}$H$_{54}$O$_6$P$_2$; 800,3396; Found: 800.3017.

Example 5A

Hydrocyanation of 3-Pentenenitrile with Ligand "C"/Ni(o-TTP)$_2$(C$_2$H$_4$); ZnCl$_2$promoter Ligand "C", 337 mg, 0.111 g of Ni(o-TTP)$_2$ (C$_2$H$_4$), and 20 mg of ZnCl$_2$ were dissolved in 5 ml of 3PN. The mixture was treated with HCN at a nitrogen flow rate of 30 ml/min at 70° C. for one hour. GC analysis indicated 52.4% ADN, 11.3% MGN and 1.6% ESN (selectivity to ADN: 80%).

Example 6

Synthesis of the ligand of Formula II where each R$^2$ is isopropyl, each R$^{2'}$ is H, each R$^1$ and R$^{5'}$ is —CH$_3$, and X is —C(H)(CH$_3$)—(Ligand "D"))

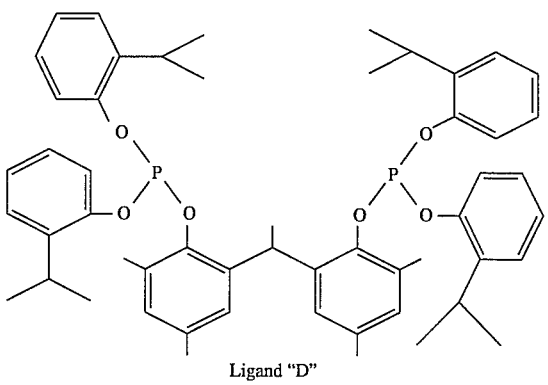

Ligand "D"

To 2 g of the chlorodite derived from PCl$_3$ and 2-isopropylphenol in 20 ml of toluene there was added 803 mg of 2,2'-ethylidenebis(4,6-dimethylphenol), prepared according to Yamada et al., Bull. Chem. Soc. Jpn., 62, 3603 (1989), and 0.900 g of NEt$_3$ in 20 ml of toluene. The mixture was stirred overnight, filtered through Celite®, and washed with toluene. The solvent was removed to give 2.603 g of the desired product as a very light-yellow oil $^{31}$P {1H} (121.4 MHz, C$_6$D$_6$): 133.53. Also, minor peaks due to impurities at 133.19, 131.25 and 130.36, 127.59 and 105.81 ppm. FBMS calculated for M+H: 871.43; Found: 871.40.

Example 6A

Hydrocyanation of 3-Pentenenitrile with Ligand "D"/Ni(COD)$_2$; ZnCl$_2$ promoter Ligand "D", 366 mg, 0.040 g of Ni(COD)$_2$, and 20 mg of ZnCl$_2$ were dissolved in 5 ml of 3PN. The mixture was treated with HCN at a nitrogen flow rate of 30 ml/min at 70° C. for one hour. GC analysis indicated 55.6% ADN, 7.8% MGN and 1.4% ESN (selectivity to ADN: 86%).

Example 7

Synthesis of the ligand of Formula II were each R$^2$ is isopropyl, R$^{2'}$ is methyl, R$^1$ and R$^{5'}$ are H, and X is —CH$_2$— (Ligand "E")

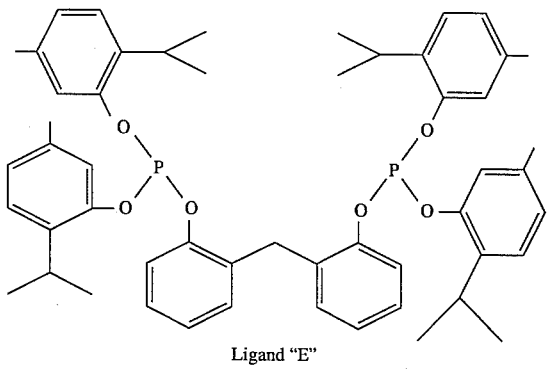

Ligand "E"

To 2 g of the chlorodite derived from PCl$_3$ and thymol in 20 ml of toluene there was added 549 mg of bis(2-hydroxyphenyl)methane and 0.910 g of NEt$_3$ in 20 ml of toluene. The mixture was stirred overnight, filtered through Celite®, and washed with toluene. The solvent was removed to give 2.379 g of the desired product as a light yellow oil. $^{31}$P {1H} (121.4 MHz, C$_6$D$_6$): 131.69. Also, hour peaks due to impurities at 132.24 and 130.9. FBMS: calculated C$_{53}$H$_{26}$O$_6$P$_2$: 856.41; Found: 855.63.

Example 7A

Hydrocyanation of 3-Penetenenitrile with Ligand "E"/Ni(COD)$_2$; ZnCl$_2$ promoter Ligand "E", 360 mg, and 0.040 g of Ni(COD)$_2$ were dissolved in 5 ml of THF. The solvent was removed, and 20 mg of ZnCl$_2$ and 5 ml of 3PN were added. The mixture was treated with HCN at a nitrogen flow rate of 30 ml/min at 70° C. for one hour. GC analysis indicated 5.8% ADN, 1.4% MGN and 0.2% ESN (selectivity to ADN: 78%).

Example 7B

Hydrocyanation of 3-Pentenenitrile with Ligand "E"/Ni(COD)$_2$; ZnCl$_2$ promoter Ligand "E", 360 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 70° C. for two hours. GC analysis indicated 27.4% ADN, 5.3% MGN, and 0.7% ESN (selectivity to ADN: 82.1%).

Example 8

Synthesis of the ligand of Formula II where each R$^2$ is isopropyl, each R$^1$ is Cl, R$^{2'}$ and R$^{5'}$ are H, and X is —CH$_2$— (Ligand "F")

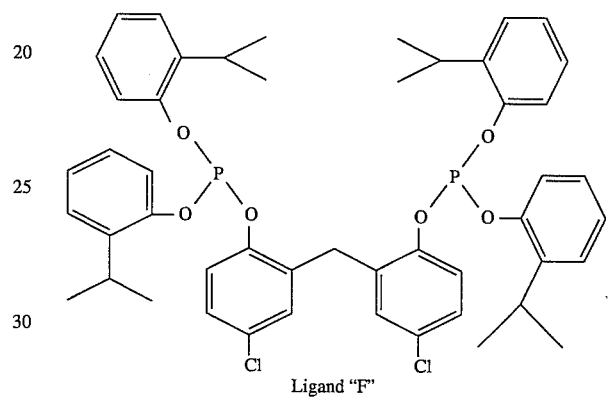

Ligand "F"

To 2 g of the phosphochloridite derived from PCl$_3$ and 2-isopropylphenol in 20 ml of toluene there was added 799 mg of 2,2'-methylenebis(4-chlorophenol) and 900 mg of NEt$_3$ in 20 ml of toluene. The mixture was stirred overnight, filtered through Celite®, and washed with toluene. The solvent was removed, to give 2,678 g of the desired product as a light-yellow opaque oil. $^{31}$P {1H} (121.4 MHz, C$_6$D$_6$): 131.6. $^1$H NMR (C$_6$D$_6$): 4.16 (s, 2H), 3,51(m, 4H), 1.3 (d, 24H) along with aromatic resonances and a little toluene. FBMS: calculated M+H: 869.27; Found: 868.96.

Example 8A

Hydrocyanation of 3-Pentenenitrile with Ligand "F"/Ni(o-TTP)$_2$(C$_2$H$_4$); ZnCl$_2$ promoter Ligand "F", 337 mg, 0.111 g of Ni(o-TTP)$_2$(C$_2$H$_4$), and 20 mg of ZnCl$_2$ were dissolved in 5 ml of 3PN. The solution was treated with HCN at a nitrogen flow rate of 30 ml/min at 70° C. for one hour. After this time, GC analysis indicated 23.6% ADN, 5.3% MGN and 1.2% ESN (selectivity to ADN: 79%).

Example 8B

Hydrocyanation of 3-Pentenenitrile with Ligand "F"/Ni(COD)$_2$; ZnCl$_2$ promoter Ligand "F", 365 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 70° C. for two hours. GC analysis indicated 51.4% ADN, 11.5% MGN, and 2.4% ESN (selectivity to ADN: 82.6%).

Example 9

Synthesis of the ligand of Formula II where each $R^2$ is isopropyl; each $R^{2'}$ para to $R^2$ is methyl, each $R^1$ is Cl, each $R^{5'}$ is H, and X is —$CH_2$— (Ligand "G")

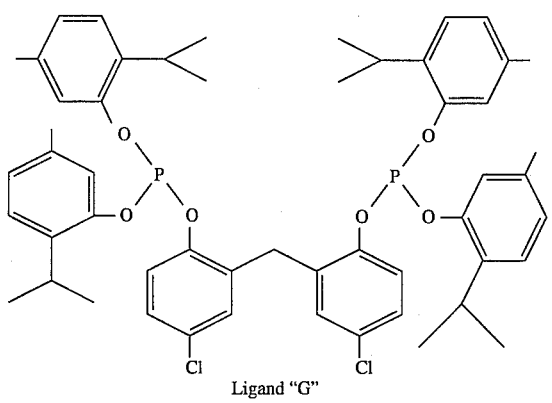

Ligand "G"

To 1.42 g of the chlorodite derived from $PCl_3$ and 2-isopropylphenol in 20 ml of toluene there was added 523 mg of 2,2'-methylenebis(4-chlorophenol) and 0.607 g of $NEt_3$ in 20 ml of toluene. The mixture was stirred overnight, filtered through Celite®, and washed with toluene. The solvent was removed to give 2.07 g of the desired product as a colorless oil. $^{31}P$ {1H} (121.4 MHz, $C_6D_6$): 131.87. FBMS: calculated M+H (M=$C_{53}H_{60}O_6P_1Cl_2$): 925.33; Found: 925.25.

Example 9A

Hydrocyanation of 3-Petenenitrile with Ligand "G"/Ni(COD)$_2$; ZnCl$_2$ promoter Ligand "G", 389 mg, and 40 mg of Ni(COD)$_2$ were dissolved in 5 ml of THF. The solvent was removed, and 5 ml of 3PN and 20 mg of ZnCl$_2$ were added. The mixture was treated with HCN at a nitrogen carrier gas flow rate of 30 ml/min at 70° C. for one hour. GC analysis indicated 6.1% ADN, 1.7% MGN and 0.25% ESN (selectivity to ADN: 76%).

Example 9B

Hydrocyanation of 3-Pentenenitrile with Ligand "G"/Ni(COD)$_2$; ZnCl$_2$ promoter Ligand "G", 389 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 79° C. for two hours. GC analysis indicated 21.2% ADN, 3.1% MGN, and 0.5% ESN (selectivity to ADN: 82.7%).

Example 10

Synthesis of the Ligand of Formula III, where each $R^2$ is isopropyl, each $R^{2'}$ and $R^{5'}$ is H, and X is —CH(p-methoxyphenyl)- (Ligand "H")

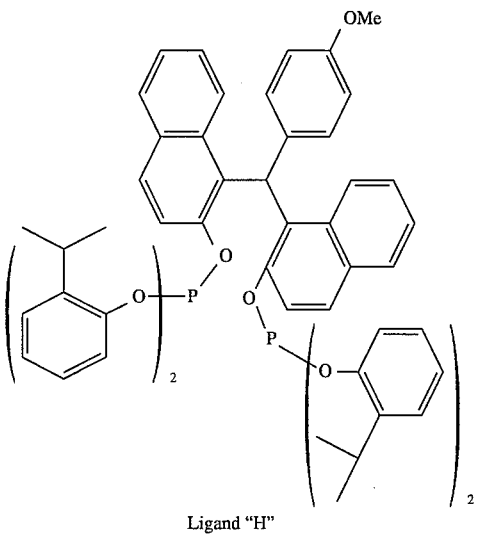

Ligand "H"

To 2 g of the chlorodite derived from $PCl_3$ and 2-isopropylphenol in 20 ml of toluene was added 1.207 g of commercial p-anisylidene 1,1'-(bis(2-naphthol)) and 1.01 g of the $NEt_3$ in 20 ml of toluene. The mixture was stirred overnight, filtered through Celite®, and washed with toluene. The solvent was removed, to give 2.916 g of the desired product as a light-yellow oil. $^{31}P$ {1H} (121.4 MHz, $C_6D_6$): 130.10. Also, a minor peak due to an impurity at 132.52 ppm.

Example 10A

Hydrocyanation using Ligand "H"

Ligand "H", 423 mg, 0.040 g of Ni(COD)$_2$, and 20 mg of ZnCl$_2$ were dissolved in 5 ml of 3PN. The mixture was treated with HCN at a nitrogen flow rate of 30 ml/min at 70° C. for one hour. GC analysis indicated 16.9% ADN, 2.8% MGN and 0.5% ESN (selectivity to ADN: 83%).

Example 10B

Hydrocyanation using Ligand "H"

Ligand "H", 423 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 70° C. for two hours. GC analysis indicated 36.8% ADN, 6.6% MGN, and 1.0% ESN (selectivity to ADN: 82.6%).

Example 11

Synthesis of the Ligand of Formula II where each $R^2$ is isopropyl; each $R^{2'}$ para to $R^2$, $R^1$ and $R^{5'}$ is methyl, and X is —CH(CH$_3$)— (Ligand "I")

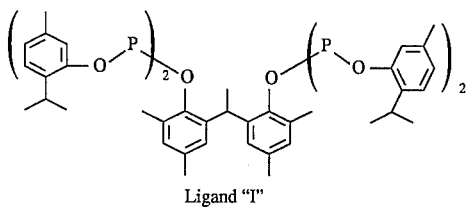

Ligand "I"

To 2 g of the chlorodite derived from PCl$_3$ and thymol in 20 ml of toluene there was added 0.741 g of 2,2'-ethylidenebis(4,6-dimethylphenol), prepared according to Yamada et al., Bull. Chem. Soc. Jpn., 62, 3603 (1989), and 1.0 g of NEt$_3$ in 20 ml of toluene. The mixture was stirred overnight, filtered through Celite®, and washed with toluene. The solvent removed to give 2,427 g of the desired product as a light yellow oil. $^{31}$P {1H} (121.4 MHz, C$_6$D$_6$): 135.15. Also, minor peaks due to impurities at 137.10, 132.5, 132.0 and 106.4 ppm. FBMS: calculated for M+H: 927.48; Found: medium-intensity ion-cluster at 925.41.

Example 11A

Hydrocyanation using Ligand "I"

Ligand "I", 389 mg, 0.040 g of Ni(COD)$_2$, and 20 mg of ZnCl$_2$ were dissolved in 5 ml of 3PN. The mixture was treated with HCN at a nitrogen carrier gas flow rate of 30 ml/min at 70° C. for one hour. GC analysis indicated 31% ADN, 2.7% MGN and 0.4% ESN (selectivity to ADN: 91%).

Example 11B

Hydrocyanation using Ligand "I"

Ligand "I", 389 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 70° C. for two hours. GC analysis indicated 48.3% ADN, 4.2% MGN, and 0.5% ESN (selectivity to ADN: 91.1%).

Example 12 synthesis of the Ligand of Formula II where each $R^2$ is isopropyl, each $R^{2'}$ is H, each $R^1$ and $R^{5'}$ is methyl, and X is —CH(CH$_2$CH$_3$)— (Ligand "J")

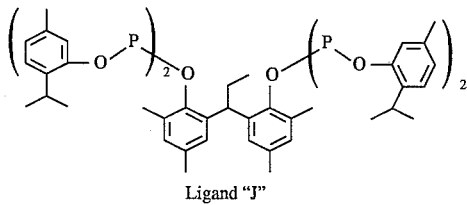

Ligand "J"

To 2 g of the chlorodite derived from PCl$_3$ and 2-isopropylphenol in 20 ml of toluene there was added 0.845 g of 2,2'-propylidenebis(4,6-dimethylphenol) (prepared according to Yamada et al., loc. cit.) and 1.0 g of NEt$_3$ in 20 ml of toluene. The mixture was stirred overnight and filtered through Celite®, and washed with toluene. The solvent was removed, to give 2.77 g of the desired product as a yellow oil. $^{31}$P {1H} (121.4 MHz, C$_6$D$_6$): 134.68. Also, minor peaks due to impurities at 136.22, 132.26, 128.6 and 105.29 ppm. FBMS: calculated for M+H: 885.44; Found: 885.39.

Example 12A

Hydrocyanation using Ligand "J"

Ligand "J", 372 mg, 0.040 g of Ni(COD)$_2$, and 20 mg of ZnCl$_2$ were dissolved in 50 ml of 3PN. The mixture was treated with HCN at a nitrogen carrier gas flow rate of 30 ml/min at 70° C. for one hour. GC analysis indicated 67% ADN, 7.2% MGN and 0.9% ESN (selectivity to ADN: 89%).

Comparative Examples 13—13B Diphenylmethane Backbone Comparative Example 13

Synthesis of the ligand of Formula II where each $R^2$ and $R^{2'}$ para to $R^2$ is t-butyl, each $R^1$ and $R^{5'}$ is H, and X is —CH$_2$— (Ligand "J2")

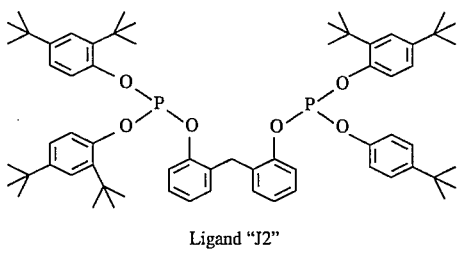

Ligand "J2"

To 2 g of the chlorodite derived from PCl$_3$ and 2,4-di-t-butylphenol in 20 ml of toluene was added 420 mg of bis(2-hydroxyphenyl)methane and 607 mg of NEt$_3$ in 20 ml of toluene. The mixture was stirred overnight and filtered through Celite®, and washed with toluene. The solvent removed to give 2.238 g of the desired product as a pale yellow oil. $^{31}$P {1H} (121.4 MHz, C$_6$D$_6$); 131.35. Also, minor peaks due to impurities at 132.6, 132.0, 131.7, 131.6, 130.3, and 121.8. ppm.

Comparative Example 13A

Hydrocyanations of 3-Pentenenitrile with Ligand "J2"/Ni(o-TTP)$_2$($_2$H$_4$), where o-TTP is P(O-o-C$_6$H$_4$CH$_3$)$_3$; ZnCl$_2$ promoter Ligand "J2", 454 mg, 0.111 g of Ni(o-TTP)$_2$(C$_2$H$_4$), and 20 mg of ZnCl$_2$ were dissolved in 5 ml of 3PN. The mixture was treated with HCN at a nitrogen carrier gas flow rate of 30 ml/min at 70° C. for one hour. GC analysis indicated 2.0% ADN, 0.8% MGN and 0.2% ESN (selectivity to ADN: 67%).

Comparative Example 13B

Hydrocyanation with Ligand "J2"/Ni(COD)$_2$

Ligand "J2", 454 mg, 0.040 g of Ni(COD)$_2$, and 20 mg of ZnCl$_2$ were dissolved in 5 ml of 3PN. The mixture was treated with HCN at a nitrogen carrier gas flow rate of 30 ml/min at 70° C. for one hour. After this time, GC analysis indicated 0.9% ADN, 0.4% MGN and 0.2% ESN.

Example 14

Synthesis of the Ligand of Formula II where each $R^2$ is isopropyl, each $R^{2'}$, $R^{5'}$ and $R^1$ is H, and X is —O— (Ligand "K")

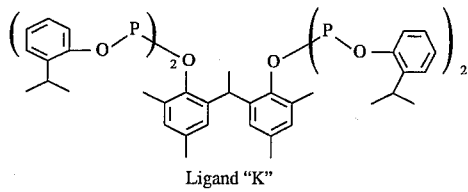

Ligand "K"

To 2 g of the chlorodite derived from $PCl_3$ and 2-isopropylphenol in 20 ml of toluene was added 0.601 g of 2,2'-dihydroxyphenyl ether and 1.0 g of $NEt_3$ in 20 ml of toluene. The mixture was stirred overnight, filtered through Celite®, and washed with toluene. The solvent was removed to give 2.44 g of the desired product as a colorless oil. $^{31}P$ {1H} (121.4 MHz, $C_6D_6$); 131.6. Also, minor peaks due to an impurities at 132.12, and 131.8 ppm.

Example 14A

Hydrocyanation using Ligand "K"

Ligand "K", 369 mg, 0.040 g of $Ni(COD)_2$, and 20 mg of $ZnCl_2$ were dissolved in 5 ml of 3PN. The mixture was treated with HCN at a nitrogen carrier gas flow rate of 30 ml/min at 70° C. for one hour. GC analysis indicated 30% ADN, 7.1% MGN and 1.0% ESN (selectivity to ADN: 79%).

Example 14B

Hydroxycanation using Ligand "K"

Ligand "K", 337 mg, 40 mg of $Ni(COD)_2$ were dissolved in 5 ml of THF. The solvent was removed by vacuum evaporation. To the residue was added 5 ml of 3PN and 20 mg of $ZnCl_2$. The mixture was treated with HCN at a nitrogen flow rate of 12 ml/min at 70° C. for two hours. GC analysis indicated 68.2% ADN, 15.4% MGN, and 3.2% ESN (selectivity to ADN, 78.6%).

Example 15

Synthesis of the Ligand of Formula II where each $R^2$ is isopropyl, each $R^{2'}$ para to $R^2$ is methyl, each $R^{5'}$ and $R^1$ is H, and X is —O— (Ligand "L")

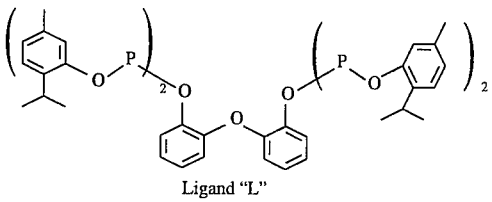

Ligand "L"

To 2 g of the chlorodite derived from $PCl_3$ and thymol in 20 ml of toluene was added 0.554 g of 2,2'-dihydroxyphenyl ether and 1.0 g of $NEt_3$ in 20 ml of toluene. The mixture was stirred overnight, filtered through Celite®, and washed with toluene. The solvent removed, to give 2.46 g of the desired product as a colorless oil. $^{31}P$ {1H} (121.4 MHz, $C_6D_6$): 131.81. Also, minor peaks due to impurities at 132.3 and 132.0 ppm.

Example 15A

Hydrocyanation using Ligand "L"

Ligand "L", 359 mg, 0.040 g of $Ni(COD)_2$, and 20 mg of $ZnCl_2$ were dissolved in 5 ml of 3PN. The mixture was treated with HCN at a nitrogen carrier gas flow rate of 30 ml/min at 70° C. for one hour. After this time, GC analysis indicated 55% ADN, 12.0% MGN and 1.0% ESN (selectivity to ADN: 80%).

Example 16

Synthesis of the ligand of Formula II where each $R^2$ is isopropyl, each $R^{2'}$ is H, each $R^{5'}$ and $R^1$ is methyl, and X is —$CH(CH_3)$— (Ligand "D2")

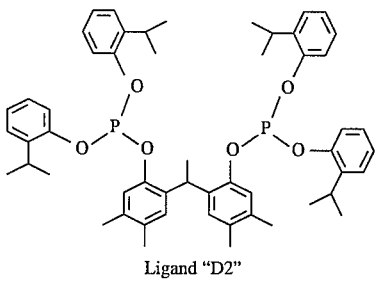

Ligand "D2"

To 2 g of the chlorodite derived from $PCl_3$ and 2-isopropylphenol in 20 ml of toluene was added 803 mg of 2,2'-ethylidenebis(4,5-dimethylphenol), prepared according to Yamada et al., op. cit., and 1 g of $NEt_3$ in 20 ml of toluene. The mixture was stirred overnight, filtered through Celite®, and washed with toluene. The solvent was removed, to give 2.541 g of the desired product as an opaque oil. $^{31}P$ {1H} (121.4 MHz, $C_6D_6$): 130.7 Minor peaks at 132.06, 131.14, and 130.14.

Example 16A

Hydrocyanation of 3-Pentenenitrile with Ligand "D2"/$Ni(COD)_2$; $ZnCl_2$ promoter 370 mg of Ligand "D2", 0.040 g of $Ni(COD)_2$, and 20 mg of $ZnCl_2$ were dissolved in 5 ml of 3PN. The mixture was treated with HCN at a nitrogen flow rate of 30 ml/min at 70° C. for one hour. GC analysis indicated 24.7% ADN, 6.0% MGN and 0.7% ESN (selectivity to ADN: 79%).

Example 16B

Hydrocyanation of 3-Pentenenitrile with Ligand "D2"/$Ni(COD)_2$; $ZnCl_2$ promoter Ligand "D2", 366 mg, 40 mg of $Ni(COD)_2$ were dissolved in 5 ml of THF. The solvent was removed by vacuum evaporation. To the residue was added 5 ml of 3PN and 20 mg of $ZnCl_2$. The mixture was treated with HCN at a nitrogen flow rate of 12 ml/min at 70° C. for two hours. GC analysis indicated 36.2% ADN, 8.7% MGN, and 1.0% ESN (selectivity to ADN: 79.0%).

Example 17

Synthesis of the ligand of Formula IV, where each $R^2$ is isopropyl, and each $R^{2'}$ and $R^{5'}$ is H (Ligand "M")

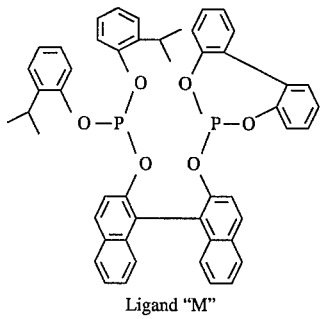

Ligand "M"

To 20 ml of a toluene solution containing 1.145 g of 2,2'-binaphthol and 1.21 g of NEt$_3$ at –40° C. was added 1.0 g of 1,1'-biphenyl- 2,2'-diyl phosphorochloridite in 20 ml of toluene. The mixture was warmed to room temperature and stirred overnight. A 20 ml toluene solution containing the chloridite derived from PCl$_3$ and 2-isopropylphenol was added thereto. After stirring for two days, the mixture was filtered through Celite®, and washed with toluene. The solvent was removed, to give 3.382 g of tan solid. $^{31}$P {1H} (121.4 MHz, C$_6$D$_6$): 145.3 δ, 131.2 δ. Also minor peaks due to impurities at 146.6, 146.4, 146.3, 132.2, and 131.0. FBMS: Found: 885.20. The FBMS data is inconsistent with the structure shown for Ligand "M" due to the possible presence of an impurity.

Example 17A

Hydrocyanation of 3-Penetenenitrile with Ligand "M"/Ni(o-TTP)$_2$(C$_2$H$_4$); ZnCl$_2$ promoter Ligand "M", 331 mg, 0.111 g of Ni(o-TTP)$_2$(C$_2$H$_4$), and 20 mg of ZnCl$_2$ were dissolved in 5 ml of 3PN. The mixture was treated with HCN at a nitrogen flow rate of 30 ml/min at 70° C. for one hour. After this time, GC analysis indicated 19.2% ADN, 3.7% MGN and 0.7% ESN (selectivity to ADN: 81%).

Example 17B

Hydrocyanation of 3-Pentenenitrile with Ligand "M"/Ni(COD)$_2$; ZnCl$_2$ promoter 344 mg of Ligand "M" and 0.040 g of Ni(COD)$_2$ and 20 mg of ZnCl$_2$ were dissolved in 5 ml of 3PN. The mixture was treated with HCN with a nitrogen flow rate of 30 ml/min at 70° C. for one hour. GC analysis indicated 41% ADN, 7.1% MGN and 1.1% ESN (selectivity to ADN: 83%).

Example 18

Synthesis of the ligand of Formula V, where each $R^2$ is isopropyl, and each $R^{2'}$ and $R^{5'}$ is H (Ligand "N")

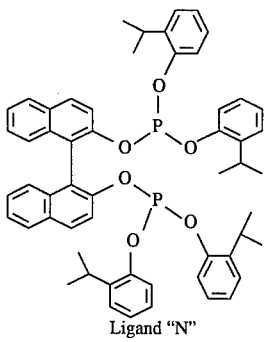

Ligand "N"

To 2 g of the phosphochloridite derived from PCl$_3$ and 2-isopropylphenol in 20 ml of toluene was added 850 mg of 1,1'-bi-2-naphthol and 1.2 g of NEt$_3$ in 20 ml of toluene. The mixture was stirred overnight, filtered through Celite®, and washed with toluene. The solvent was removed, to give 2.711 g of the desired product as a yellow liquid. $^{31}$P {1H} (121.4 MHz, C$_6$D$_6$): 131.51. FBMS calculated for M+1 for the desired product C$_{56}$H$_{56}$O$_6$P$_2$: 887.36; Found 887.37.

Example 18A

Hydrocyanation of 3-Pentenenitrile with Ligand "N"/Ni(COD)$_2$; ZnCl$_2$ promoter Ligand "N", 373 mg, and 0.040 g of Ni(COD)$_2$ were dissolved in 5 ml of 3PN containing 20 mg of ZnCl$_2$. The mixture was treated with HCN at a nitrogen flow rate of 30 ml/min at 70° C. for one hour. GC analysis indicated 21.5% ADN, 3.3% MGN and 0.5% ESN (selectivity to ADN: 85%).

Example 18B

Hydrocyanation of 3-Pentenenitrile with Ligand "N"/Ni(COD)$_2$; ZnCl$_2$ promoter Ligand "N", 373 mg, 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 30 ml/min at 70° C. for one hour. GC analysis indicated 58.9% ADN, 9.2% MGN, and 1.1% ESN (selectivity to ADN: 83.3%).

Example 19

Synthesis of the ligand of Formula V, where each $R^2$ is isopropyl, each $R^{2'}$ para to $R^2$ is methyl and the other $R^{2'}$ is H, and each $R^{5'}$ is H (Ligand "O")

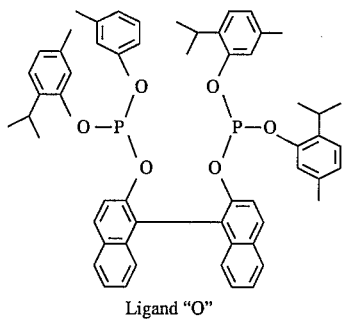

Ligand "O"

To 20 ml of toluene solution containing 2.0 g of the phosphorochloridite derived from $PCl_3$ and thymol were added 0.785 g of 1,1'-bi2-naphthol and 0.910 g of $NEt_3$ in 20 ml of toluene. The mixture was stirred overnight. The mixture was filtered through Celite®, and washed with toluene. The solvent was removed, to give 2.569 g of an orange oil. $^{31}P$ {1H} (121.4 MHz, $C_6D_6$): 131.246. Also minor peaks due to impurities at 145.73 and 132.31. FBMS: Found: 941.64; calculate for $C_{60}H_{64}O_6P_2$: 942.42.

Example 19A

Hydrocyanations of 3-Pentenenitrile with Ligand "O"/Ni(COD)$_2$; $ZnCl_2$ promoter Ligand "O", 395 mg, 0.040 g of Ni(COD)$_2$, and 20 mg of $ZnCl_2$ were dissolved in 5 ml of 3PN. The mixture was treated with HCN at a nitrogen flow rate of 30 ml/min at 70° C. for one hour. GC analysis indicated 63% ADN, 8.0% MGN and 0.8% ESN (selectivity to ADN: 88%).

Comparative Example 20

Synthesis of the ligand of Formula V, where each $R^2$ and $R^{2'}$ para to $R^2$ is t-butyl, other $R^{2'}$ is H and each $R^{5'}$ is H (Ligand "P")

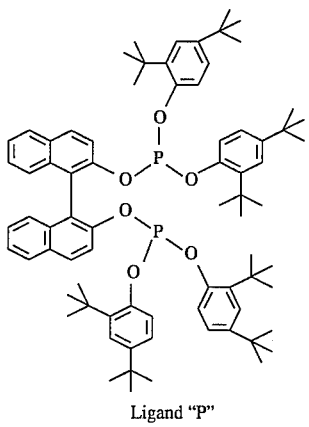

Ligand "P"

Phosphorus trichloride (0.55 g, 4.0 mmols) was dissolved in toluene (10 ml) and cooled in an ice/salt bath. 2,6-Di-t-butyl phenol (1.65 g, 8.0 mmols) and triethylamine (2.1 ml; 15 mmols) were dissolved in toluene (10 ml). This solution was added dropwise to the cold $PCl_3$ solution. After 30 min, the mixture was heated to reflux for 75 minutes. The mixture was again cooled in the ice bath, and a solution of 1,1'-bi(2-naphthol) (0.57 g; 2.0 mmol) in toluene was added dropwise. The reaction mixture was heated to reflux for 1.5 hours. The mixture was cooled, and the solids were removed by filtration. The solvent was removed in vacuo, leaving a sticky yellow solid. Recrystallization from acetonitrile was unsuccessful because the material was fairly soluble. The acetonitrile was removed to give a pale yellow solid. $^{31}P$ NMR (CDCl$_3$): δ129.7. Also, small peaks at 130.8 and 145.6 due to impurities.

Comparative Example 20A

Hydrocyanation using Ligand P

Ligand "P", 490 mg, 0.040 g of Ni(COD)$_2$, and 20 mg of $ZnCl_2$ were dissolved in 5 ml of 3PN. The mixture was treated with HCN at a nitrogen carrier gas flow rate of 30 ml/min at 70° C. for one hour. GC analysis indicated 3.7% ADN, 0.7% MGN and 0.4% ESN (selectivity to ADN: 77%).

Examples 22–31

Hydrocyanation of 3-Pentenenitrile

Table 1 shows hydrocyanations using a variety of ligands of the invention, prepared in accordance with the general procedures described in the previous examples. The specific conditions for each hydrocyanation are described as Method A, B or C.

Comparative Examples A-C2

Hydrocyanation of 3-Pentenenitrile using p-tritolylphosphite

Comparative Example A

Compares to Method A of Table 1

To 5 ml of THF was added 0.296 g (0.84 mmoles) of p-tritolylphosphite and 0.040 g (0.14 mmoles) of Ni(COD)$_2$. The solvent was removed by vacuum evaporation. To the residue was added 5 ml of 3PN and 20 mg of $ZnCl_2$. The mixture was treated with HCN at a nitrogen flow rate of 30 ml/min at 70° C. for one hour. GC analysis indicated 37.5% ADN, 8.4% MGN and 1.3% ESN (selectivity to ADN: 79.4%)

Comparative Example B

Compares to Method B of Table 1

To 5 ml of 3PN was added 0.306 g (0.89 mmoles) of p-tritolylphosphite and 0.115 g (0.14 mmoles) of (oTTP)$_2$Ni(ethylene) (oTTP=o-tritolylphosphite) and 0.020 g of $ZnCl_2$. The mixture was treated with HCN at a nitrogen flow rate of 30 ml/min at 70° C. for one hour. GC analysis indicated 28.6% AND, 5.9% MGN and 0.9% ESN (selectivity to ADN: 80.7%).

Comparative Example C1

Compares to Method C of Table 1

296 mg of p-tritolylphosphite and 40 mg of Ni(COD)$_2$ were dissolved in 5 ml of THF. The solvent was removed by vacuum evaporation. To the residue was added 5 ml of 3PN and 20 mg of ZnCl$_2$. The mixture was treated with HCN at a nitrogen flow rate of 12 ml/min at 70° C. for two hours. GC analysis indicated 22.7% ADN, 5.1% MGN, and 0.8% ESN (selectivity to ADN: 79.4%).

Comparative Example C2

Compares to Method C of Table 1

To 5 ml of 3PN was added 0.099 g (0.28 mmoles) of p-tritolylphosphite, 0.205 g (0.14 mmoles) of tetrakis(p-tritolylphosphite)nickel and 20 mg of ZnCl$_2$. The mixture was treated with HCN at a nitrogen flow rate of 12 cc/min. After 1 hr of reaction, GC analysis indicated 26.5% ADN, 5.9% MGN and 0.8% ESN (selectivity to ADN: 79.8%). After 2 hr of reaction, GC analysis indicated 27.6% ADN, 6.1% MGN, 0.9% ESN (selectivity to ADN: 79.8%)

TABLE 1

| Example No. | Ligand Structure | Conversion | % ADN | Hydrocyanation Method |
|---|---|---|---|---|
| 22 | 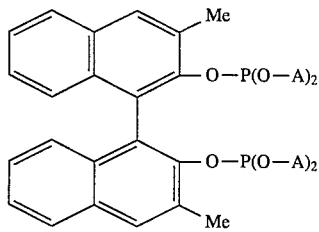 | 19.0 | 92.4 | A |
| 23 | 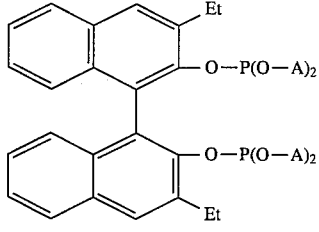 | 6.7 | 88.3 | A |
| 24 | 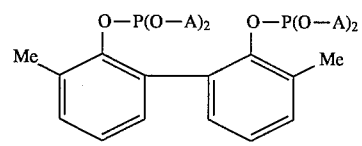 | 28.7 | 91.6 | A |
| 25 | 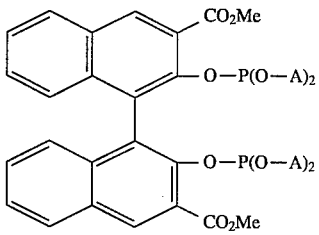 | 6.3 | 91.2 | A |
| 26 | 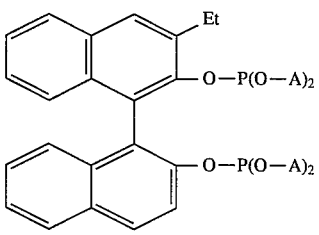 | 77.5 | 90.1 | A |

TABLE 1-continued
| Example No. | Ligand Structure | Conversion | % ADN | Hydrocyanation Method |
|---|---|---|---|---|
| 27 | 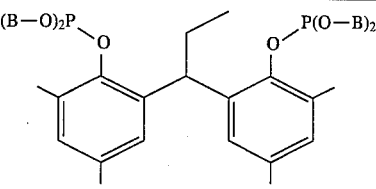 | 25.9 | 89.1 | C |
| 28 | 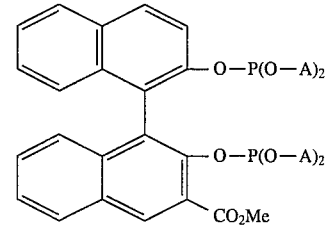 | 24.3 | 89.9 | A |
| 29 | 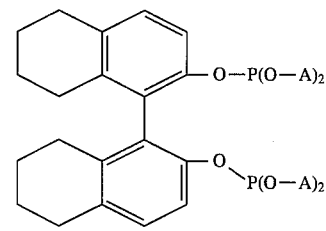 | 41.0 | 83.9 | B |
| 30 | 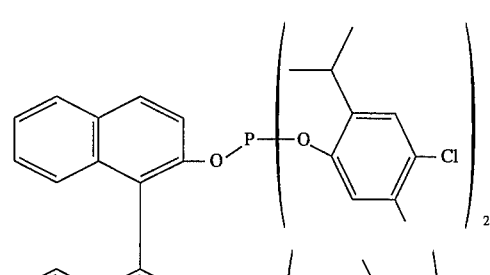 | 46.9 | 84.8 | A |
| 31 | 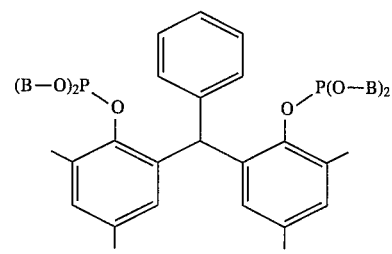 | 15.8 | 86.1 | C |
Method A: 0.42 mmoles ligand, 0.14 mmoles Ni(COD)$_2$ in 5 ml THF. Remove solvent. 5 ml 3PN and 20 mg ZnCl$_2$. HCN at 30 ml/min for 1 hr.
Method B: 0.42 mmoles ligand, 0.14 mmoles Ni(COD)$_2$ in 5 ml 3PN and 20 mg ZnCl$_2$. HCN at 30 ml/min for 1 hr.

Method C: 0.42 mmoles ligand, 0.14 mmoles Ni(COD)$_2$ in 5 ml THF. Remove solvent. 5 ml 3PN and 20 mg ZnCl$_2$. HCN at 12 ml/min for 2 hours.

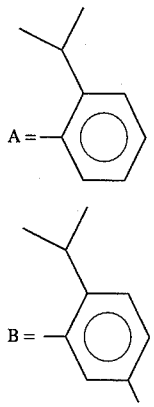

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. A hydrocyanation process comprising reacting an acyclic, aliphatic, monoethylenically unsaturated compound in which the ethylenic double bond is not conjugated to any other olefinic group in the molecule, or a monoethylenically unsaturated compound in which the ethylenic double bond is conjugated to an organic ester group, with a source of HCN in the presence of a catalyst composition comprising a Lewis acid, a zero-valent nickel, and at least one multidentate phosphite ligand selected from the group represented by the following Formulas I, II, III, IV, V, VI and VII:

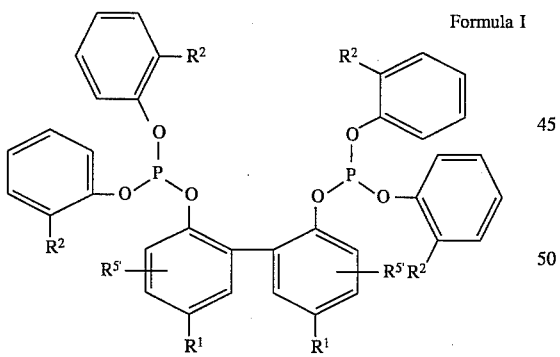

Formula I

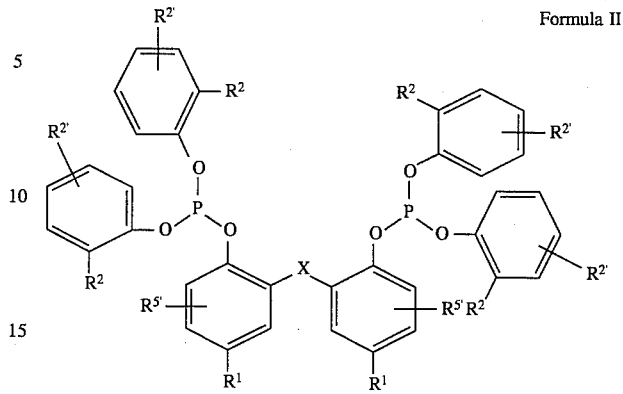

Formula II

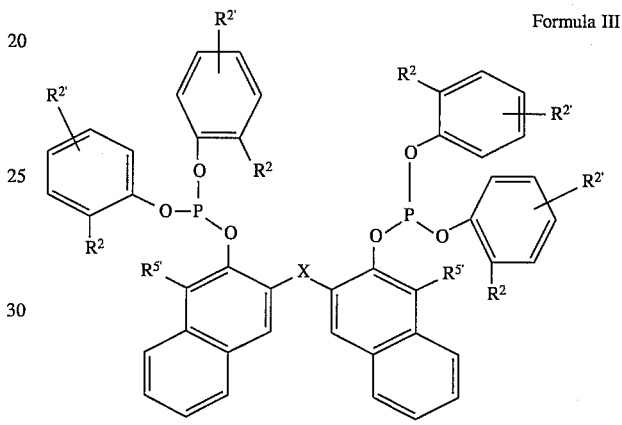

Formula III

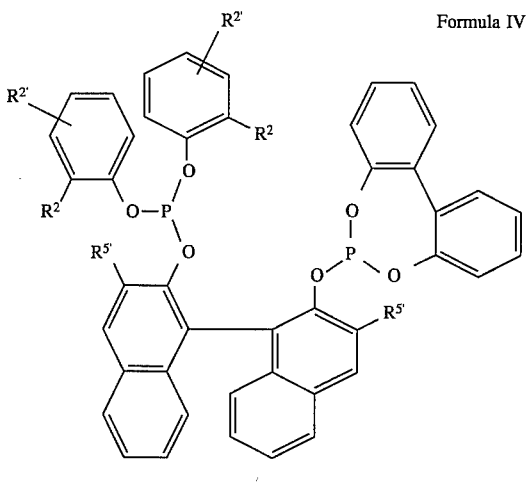

Formula IV

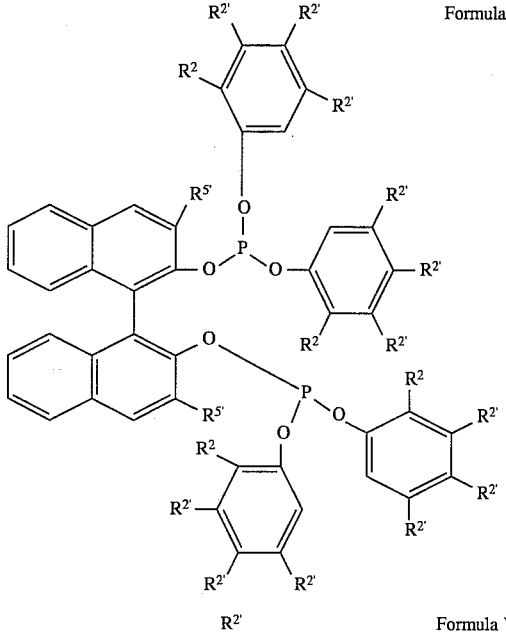

Formula V

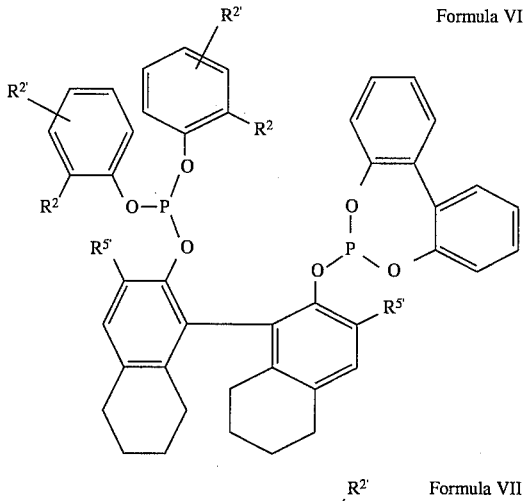

Formula VI

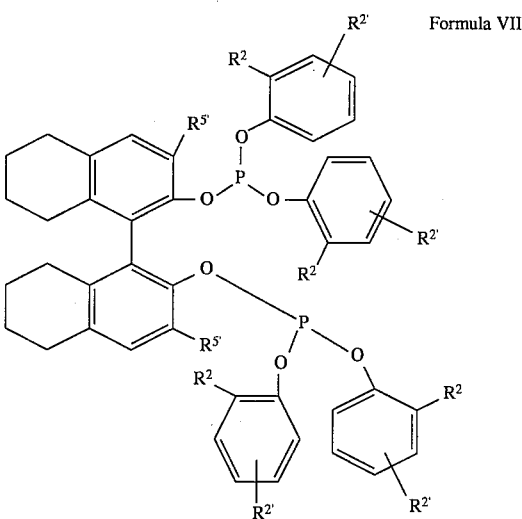

Formula VII wherein each $R^1$ is independently, H, halogen, a $C_1$ to $C_6$ alkyl, or $OR^3$ wherein $R^3$ is a $C_1$ to $C_6$ alkyl;

each $R^2$ is independently a secondary or tertiary hydrocarbyl of 3 to 6 carbon atoms;

each $R^{2'}$ is independently H, halogen, $OR^3$ wherein $R^3$ is a $C_1$ to $C_6$ alkyl or a primary, secondary or tertiary hydrocarbyl of 1 to 6 carbon atoms; for Formulas II, III, IV, VI and VII, $R^{2'}$ is at either the meta or para position to the oxygen;

each $R^{5'}$ is independently H or a primary or secondary hydrocarbyl of 1 to 3 carbon atoms in either the ortho or meta position to the oxygen or $CO_2R^{3'}$ where $R^{3'}$ is a $C_1$ to $C_4$ alkyl; and each X is independently O or $CH(R^{4'})$, wherein $R^{4'}$ is H, a substituted phenyl, or a $C_1$ to $C_6$ alkyl;

with the proviso that the terms "secondary" and "tertiary" herein refer to the carbon atom bonded to an aromatic ring;

and with the further proviso that in Formulas I, II, and V at least one $R^2$ cannot be a tertiary hydrocarbyl.

2. The process of claim 1 wherein the starting ethylenically unsaturated compound is selected from the group consisting of the compounds of the following formulas VIII and X:

$$CH_3-(CH_2)_y-CH=CH-(CH_2)_x-R^4 \quad (VIII)$$

$$CH_2=CH-(CH_2)_x-R^4 \quad (X)$$

wherein $R^4$ is H, CN, $CO_2R^5$, or perfluoroalkyl;

y is an integer of 0 to 12;

x is an integer of 0 to 12 when $R^4$ is H, $CO_2R^5$ or perfluoroalkyl;

x is an integer of 1 to 12 when $R^4$ is CN; and $R^5$ is alkyl.

3. The process of claim 1 wherein the starting ethylenically unsaturated compound is selected from the group consisting of 3-pentenenitrile, 4-pentenenitrile; alkyl 2-, 3-, and 4-pentenoates, and $C_zF_{2z+1}CH=CH_2$, where z is an integer of 1 to 12.

4. The process of claim 3 wherein the starting ethylenically unsaturated compound is 3-pentenenitrile or 4-pentenenitrile.

5. The process of claim 1 which is carried out at a temperature of −25° C. to 200° C. and at a pressure of 50.6 to 1013 kPa.

6. The process of claim 5 which is carried out at atmospheric pressure and at a temperature of 0° C. to 150° C.

7. The process of claim 1 wherein the Lewis acid is selected from the group consisting of inorganic or organometallic compounds in which the cation is selected from scandium, titanium, vanadium, chromium, manganese, iron, cobalt, copper, zinc, boron, aluminum, yttrium, zirconium, niobium, molybdenum, cadmium, rhenium and tin.

8. The process of claim 7 wherein the Lewis acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(tetrahydrofuran)_2$, $TiCl_4(tetrahydrofuran)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $(phenyl)_2AlCl$, $phenylAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $CdCl_2$, $B(C_6H_5)_3$, and $(C_6H_5)_3SnX$, where $X=CF_3SO_3$, $CH_3C_6H_5SO_3$, or $(C_6H_5)_3BCN$.

* * * * *

UNITED STATES PATENT AND TRADEMARK OFFICE
CERTIFICATE OF CORRECTION

PATENT NO. : 5,512,696
DATED : April 30, 1996
INVENTOR(S) : Kreutzer et al.

It is certified that error appears in the above-identified patent and that said Letters Patent is hereby corrected as shown below:

On page 3, column 4, line 29, change "Formula" to read --Formulas--.

On page 3, column 4, line 30, change the first occurrence of "VI" to read --IV--.

On page 3, column 4, line 47, change "phosphate" to read --phosphite--.

On page 3, column 4, line 48, change "Formula" to read --Formulas--.

On page 3, column 4, line 55, change "Formula" to read --Formulas--.

On page 4, column 5, line 39, change "each $R^{2'}$ group is para to $R^2$ methyl" to read --each $R^{2'}$ group para to $R^2$ is methyl--.

On page 4, column 6, line 11, change "Z" to read --Zn--.

On page 8, column 13, line 51, change "hour" to read --minor--.

On page 8, column 14, line 40, change "2,678" to read --2.678--.

On page 8, column 14, line 42, change "3,51" to read --3.51--.

On page 9, column 15, line 65, change "79°C" to read --70°C--.

On page 10, column 17, line 22, change "2,427" to read --2.427--.

On page 10, column 17, line 52, change "synthesis" to read --Synthesis--.

UNITED STATES PATENT AND TRADEMARK OFFICE
CERTIFICATE OF CORRECTION

PATENT NO. : 5,512,696
DATED : April 30, 1996
INVENTOR(S) : Kreutzer et al.

It is certified that error appears in the above-identified patent and that said Letters Patent is hereby corrected as shown below:

On page 10, column 17, lines 55-63, change

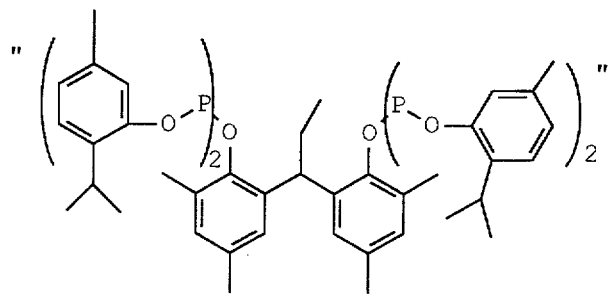

Ligand "J"

to read

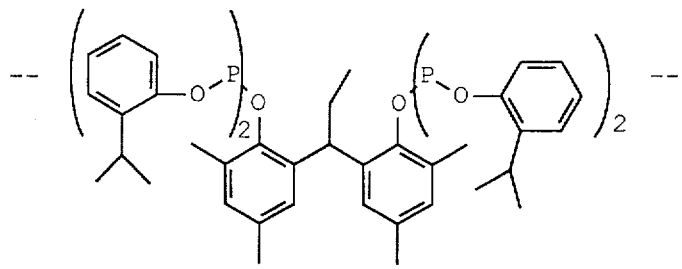

Ligand "J"

On page 10, column 18, line 14, change "50" to read --5--.

UNITED STATES PATENT AND TRADEMARK OFFICE
CERTIFICATE OF CORRECTION

PATENT NO. : 5,512,696
DATED : April 30, 1996
INVENTOR(S) : Kreutzer et al.

It is certified that error appears in the above-identified patent and that said Letters Patent is hereby corrected as shown below:

On page 11, column 19, lines 6-13, change

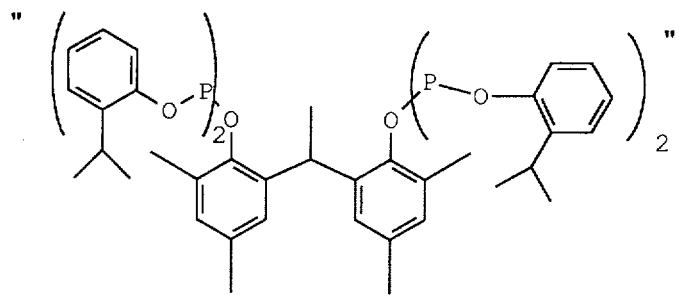

Ligand "K"

to read

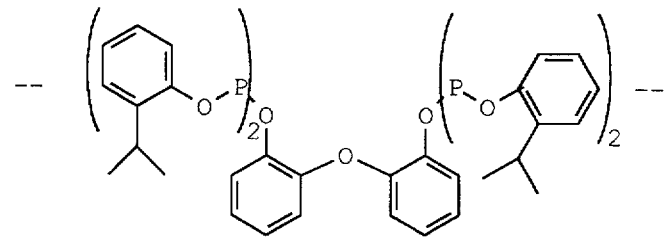

Ligand "K"

On page 13, column 23, line 22, change "1,1'-bi2-naphthol" to read --1,1'-bi-2-naphthol--.

UNITED STATES PATENT AND TRADEMARK OFFICE
CERTIFICATE OF CORRECTION

PATENT NO. : 5,512,696
DATED : April 30, 1996
INVENTOR(S) : Kreutzer et al.

It is certified that error appears in the above-identified patent and that said Letters Patent is hereby corrected as shown below:

On page 13, column 24, line 3, change "1,1'-bi(2-naphthol)" to read --1,1'-bi-(2-naphthol)--.

Signed and Sealed this

Fifth Day of August, 1997

Attest:

BRUCE LEHMAN

Attesting Officer

Commissioner of Patents and Trademarks